(12) United States Patent
Redda et al.

(10) Patent No.: US 8,476,303 B2
(45) Date of Patent: Jul. 2, 2013

(54) N-AMINOPYRROLYLMETHYLTETRA-HYDROPYRIDINES AS ANTI-CANCER AGENTS

(75) Inventors: Kinfe Ken Redda, Tallahassee, FL (US); Madhavi Gangapuram, Tallahassee, FL (US)

(73) Assignee: Florida A&M University Board of Trustees, Tallahassee, FL (US)

( * ) Notice: Subject to any disclaimer, the term of this patent is extended or adjusted under 35 U.S.C. 154(b) by 68 days.

(21) Appl. No.: 13/307,771

(22) Filed: Nov. 30, 2011

(65) Prior Publication Data

US 2013/0109724 A1 May 2, 2013

Related U.S. Application Data

(60) Provisional application No. 61/553,343, filed on Oct. 31, 2011.

(51) Int. Cl.
*A61K 31/44* (2006.01)
*C07D 401/06* (2006.01)

(52) U.S. Cl.
USPC ........................................ 514/343; 546/276.4

(58) Field of Classification Search
None
See application file for complete search history.

(56) References Cited

U.S. PATENT DOCUMENTS 7,026,476 B2 * 4/2006 Cirillo et al. .................. 544/106

* cited by examiner

*Primary Examiner* — Kamal Saeed
(74) *Attorney, Agent, or Firm* — Thomas Horstemeyer LLP

(57) ABSTRACT

The compounds herein disclosed are N-aminopyrrolylmethyltetrahydropyridine analogs that have modifications on the phenyl rings by introducing groups with various electronic properties. These derivatives of N-aminopyrrolylmethyltetrahydropyridines have been shown to have anti-proliferative activity against cells. In particular, the compounds have been found to be effective in inhibiting the proliferation of cancer cells, such as cancer cells that originated in breast tissue. Additionally, it has been shown that the novel compounds have $IC_{50}$ values against the breast cancer cells that are 6-10-fold less than the $IC_{50}$ of tamoxifen.

15 Claims, 5 Drawing Sheets

N-AMINOPYRROLYLMETHYLTETRA-HYDROPYRIDINES AS ANTI-CANCER AGENTS

CROSS-REFERENCE TO RELATED APPLICATIONS

This application claims priority to U.S. Provisional Patent Application Ser. No. 61/553,343, entitled "N-AMINOPYRROLYLMETHYLTETRAHYDROPYRIDINES AS ANTI-CANCER AGENTS" filed on Oct. 31, 2011, the entirety of which is hereby incorporated by reference.

STATEMENT REGARDING FEDERALLY SPONSORED RESEARCH OR DEVELOPMENT

This invention was made with government support under Grant No. G12 RR03020 of the National institutes of Health, National Center of Research Resources, Research Center in Minority Institutions Program of the United States government. The government has certain rights in the invention

TECHNICAL FIELD

The present disclosure is generally related to N-aminopyrrolylmethyltetrahydropyridines compounds and their use in modulating the proliferation of transformed (cancer) cells.

BACKGROUND

Cancer is a disease in which cells in the body grow out of control. Cancer and cancer cells are typically named according to the tissue in which the cells start in the breast, it is called breast cancer. Breast cancer is the second leading cause of cancer-related deaths in women today and is the most common cancer among women, excluding non-melanoma skin cancers. In 2009, an estimated 192,370 new cases of invasive breast cancer were diagnosed among women, as well as an estimated 62,280 additional cases of in situ breast cancer. In 2009, approximately 40,170 women were expected to die from breast cancer.

There is evidence that COX-2 plays a key role in tumorigenesis through stimulating epithelial cell proliferation, inhibiting apoptosis, stimulating angiogenesis, enhancing cell invasiveness, mediating immune suppression, and by increasing the production of mutagens. Studies with several other epithelial cancers involving different organ sites, e.g., breast, prostate, bladder, lung, and pancreas, suggest that COX-2 plays an important role in the pathogenesis of these cancers. NSAIDs are not only useful in the treatment of inflammatory diseases, but they can also reduce the risk of Alzheimer's disease (Andersen et al., (1995) *Neurology* 45: 1441-1444; Breitner, J. C. S. (1996) *Annu. Rev. Med.* 47: 401). NSAIDs produce their therapeutic activities through inhibition of cyclooxygenase (COX), the enzyme that makes prostaglandins (PGs). The two isozymes of COX involved in prostaglandin biosynthesis are COX-1 and COX-2. COX-1 is expressed virtually in all tissues and is responsible for the production of prostanoids critical to the maintenance of normal physiologic functions. COX-2 is usually absent from most normal cells and tissues but is expressed in pathologic states such as inflamed tissues, and tumors. It can be induced by various agents, including growth factors and tumor promoters. COX-2, therefore, represents a suitable target enzyme for antagonists that can serve as therapeutic agents inhibiting the development of cancers.

SUMMARY

Briefly described, embodiments of this disclosure, among others, encompass embodiments of a compound having the structure of formula I:

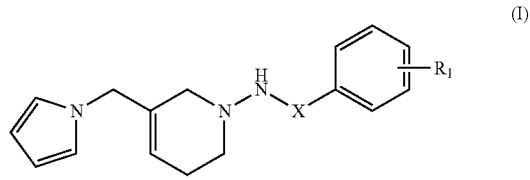

(I)

where X is a carbonyl group or a sulfonyl group; and $R_1$ can be H, an alkyl group, an alkoxy group, or an electronegative group; or a salt thereof.

In embodiments of this aspect of the disclosure, $R_1$ can be $CH_3$ or $—O—CH_3$.

In embodiments of this aspect of the disclosure, $R_1$ can be a halogen or $—NO_2$.

In one embodiment of this aspect of the disclosure, $R_1$ can be $CH_3$.

In one embodiment of this aspect of the disclosure, the compound can be selected from the group consisting of:

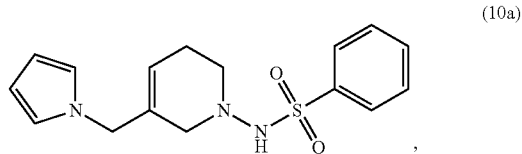

(10a)

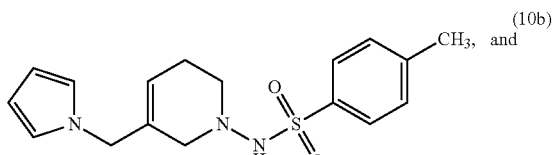

(10b)

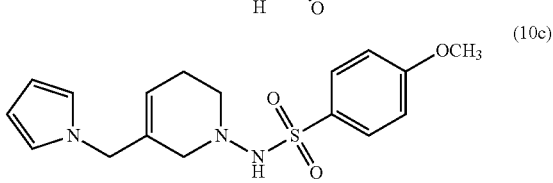

(10c)

Another aspect of the disclosure encompasses embodiments of a pharmaceutically acceptable composition comprising a compound having the structure:

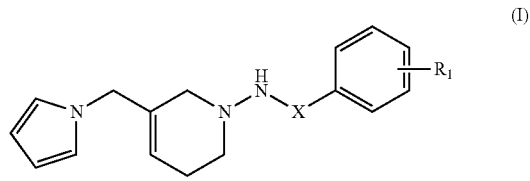

(I)

where X is a carbonyl group or a sulfonyl group; and $R_1$ can be H, an alkyl group, an alkoxy group, or an electronegative group; or a salt thereof, and a pharmaceutically acceptable carrier.

In embodiments of this aspect of the disclosure, $R_1$ can be $CH_3$ or $—O—CH_3$.

In embodiments of this aspect of the disclosure, $R_1$ can be a halogen or —$NO_2$.

In one embodiment of this aspect of the disclosure, $R_1$ can be $CH_3$.

In one embodiment of this aspect of the disclosure, the compound can be selected from the group consisting of:

In one embodiment of this aspect of the disclosure, the pharmaceutically acceptable composition can be formulated to provide an amount of the compound effective in inhibiting the proliferation of a cell cultured in vitro.

In embodiments of this aspect of the disclosure, the cell is a cancer cell.

In some embodiments of this aspect of the disclosure, the cell is a breast cancer cell.

In one embodiment of this aspect of the disclosure, the pharmaceutically acceptable composition can be formulated to provide a therapeutically effective amount of the compound for inhibiting the proliferation of a cell in vivo.

In some embodiments of this aspect of the disclosure, the cell is a cancer cell.

In one embodiment of this aspect of the disclosure, the cell is a breast cancer cell.

Still another aspect of the disclosure encompasses embodiments of a method of inhibiting the proliferation of a cell comprising contacting a cell with an effective amount of a compound having the structure:

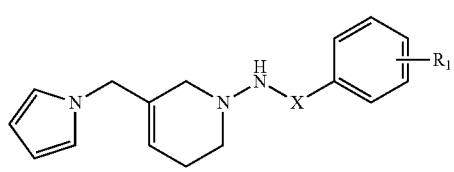

(I)

where X is a carbonyl group or a sulfonyl group; and $R_1$ can be H, an alkyl group, an alkoxy group, or an electronegative group; or a salt thereof, and a pharmaceutically acceptable carrier, thereby reducing the proliferation rate of the cell compared to the proliferation rate of a cell not in contact with the compound.

In embodiments of this aspect of the disclosure, $R_1$ can be $CH_3$ or —O—$CH_3$.

In embodiments of this aspect of the disclosure, $R_1$ can be a halogen or —$NO_2$.

In one embodiment of this aspect of the disclosure, $R_1$ can be $CH_3$.

In embodiments of this aspect of the disclosure, the compound is selected from the group consisting of:

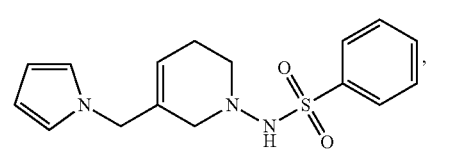

(10a)

,

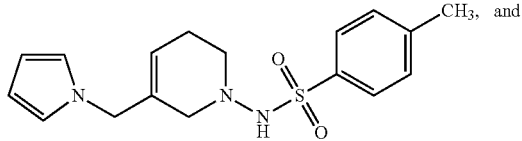

(10b)

$CH_3$, and

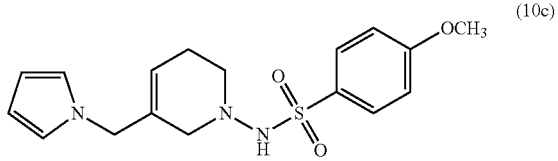

(10c)

In embodiments of this aspect of the disclosure, the cell can be a cancer cell.

In one embodiment of this aspect of the disclosure, the cell is a breast cancer cell.

In embodiments of this aspect of the disclosure, the cell is a cultured cell or a cell of an animal or human subject.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
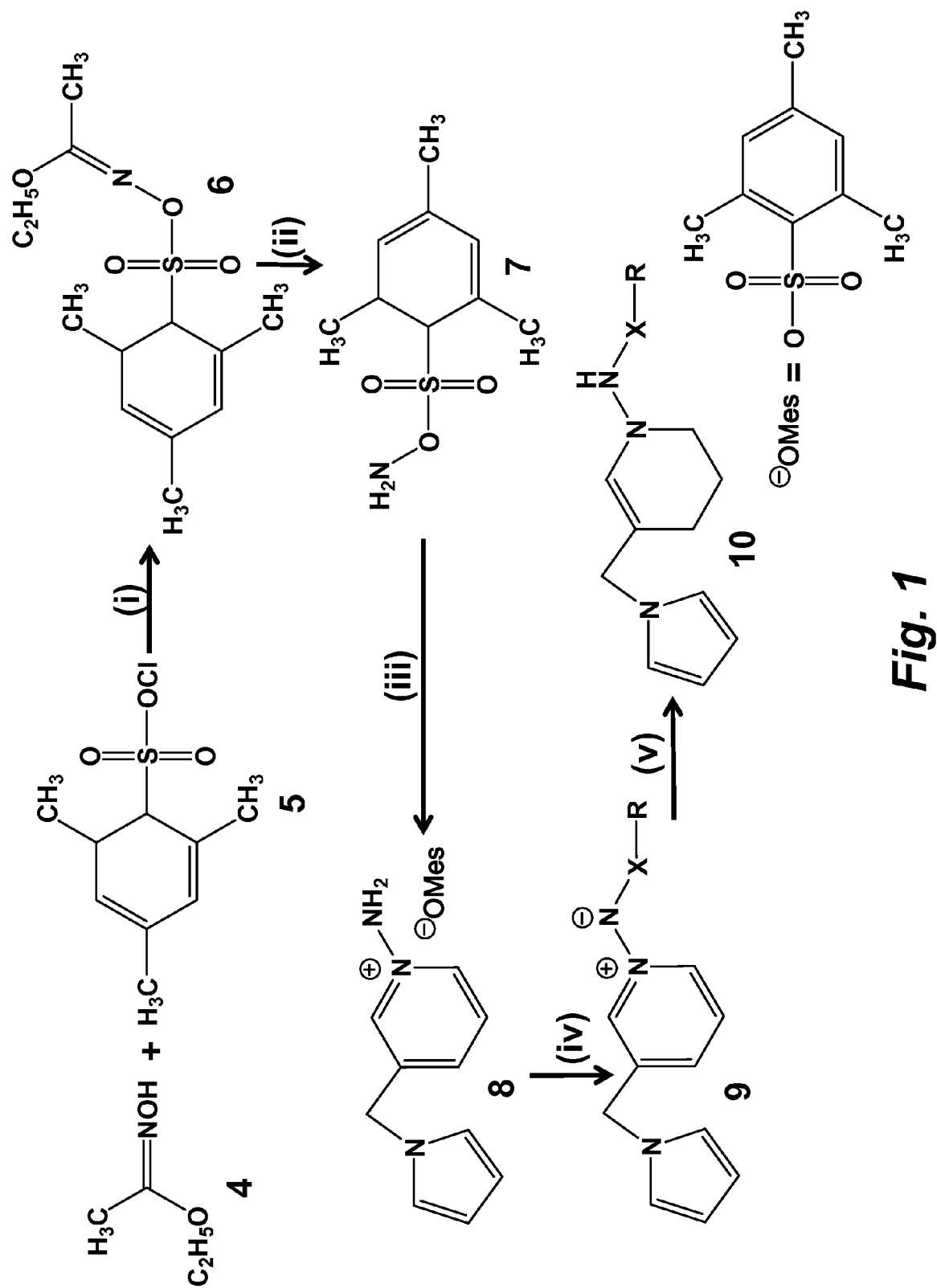
FIG. 1 shows a schema of the synthesis of substituted N-aminopyrrolylmethyltetrahydropyridines. Reaction conditions: (i) DMF, triethylamine, 0° C., 45 min; (ii) 70% $HClO_4$, p-dioxane, 0° C., 45 min; (iii) 3-((1H-pyrrol-1-yl)methyl)pyridine, $CH_2Cl_2$, 0° C., 5 h; (iv) 4-substituted acyl/sulfonyl chloride, dry THF, 70° C.; and (v) $NaBH_4$, absolute ethanol, 7 h. R can be, for example, $C_6H_5$, 4-$CH_3$—$C_6H_4$, 4-$OCH_3$—$C_6H_4$; X=$SO_2$.
Figure 2:
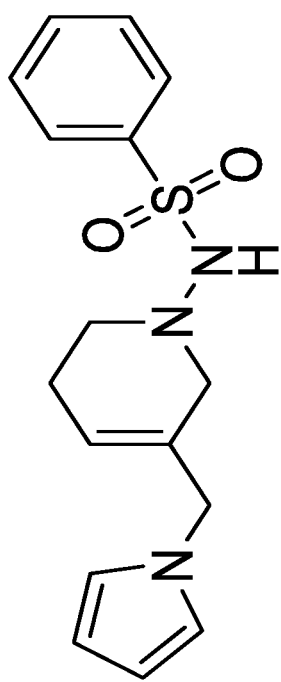
FIG. 2 illustrates the structures of compounds Redda-GM-2-50 (10a), Redda-GM-2-55 (10b), and Redda-GM-2-58 (10c).
Figure 2:
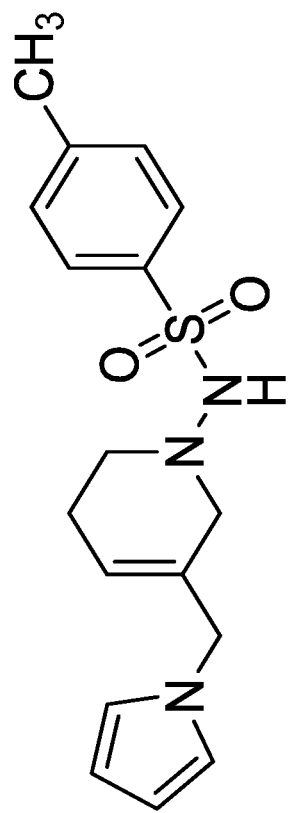
Figure 2:
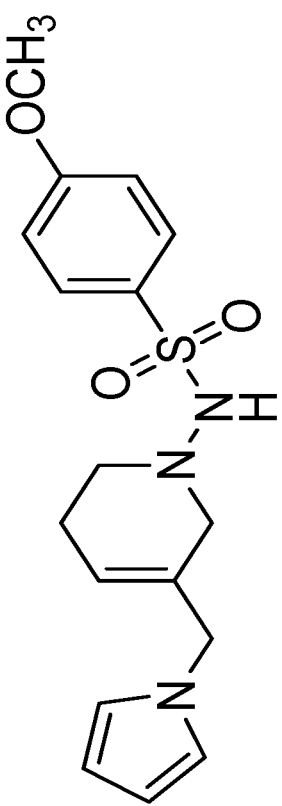
Figure 3:
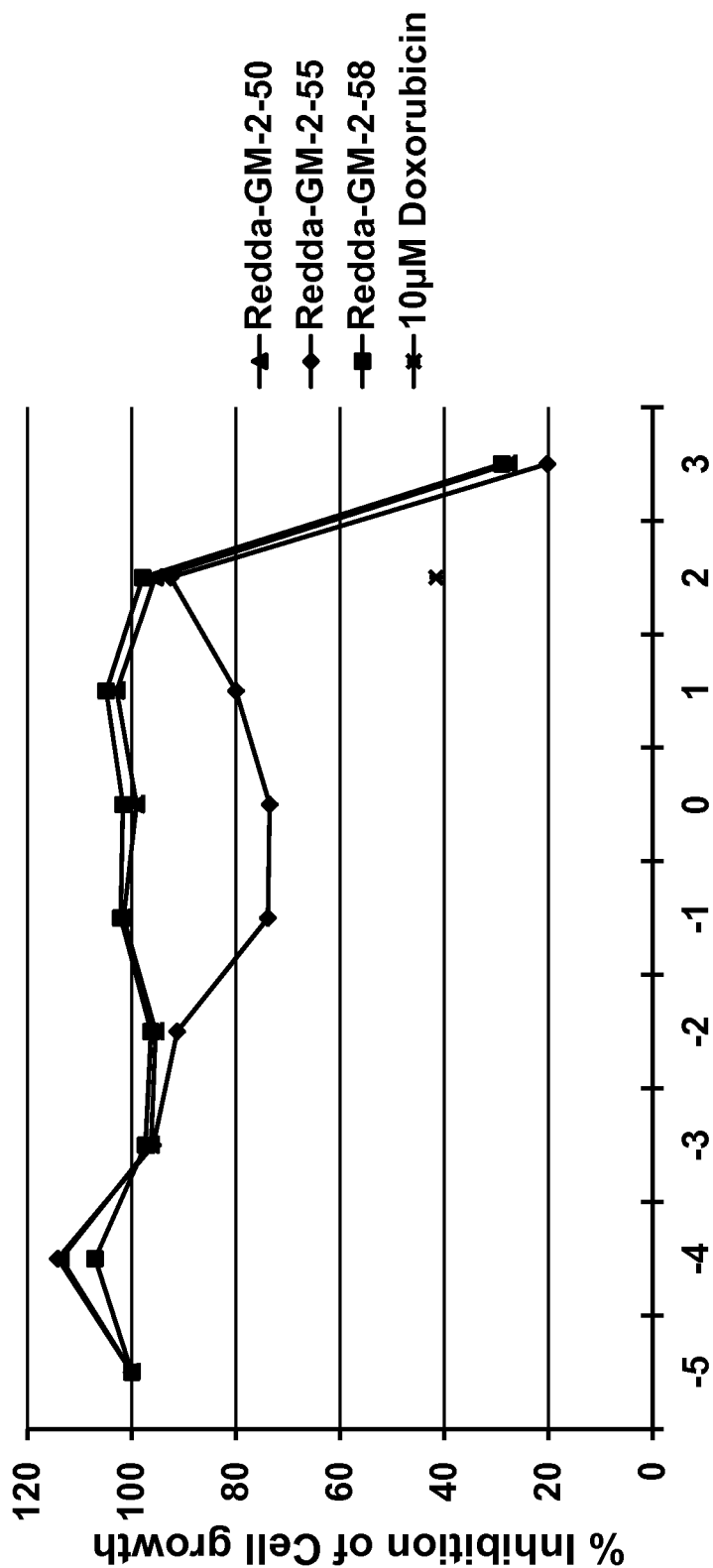
FIG. 3 is a graph illustrating the inhibition of the growth of MCF-7 cells by exposure to the compounds of the disclosure, and to tamoxifen.
Figure 4:
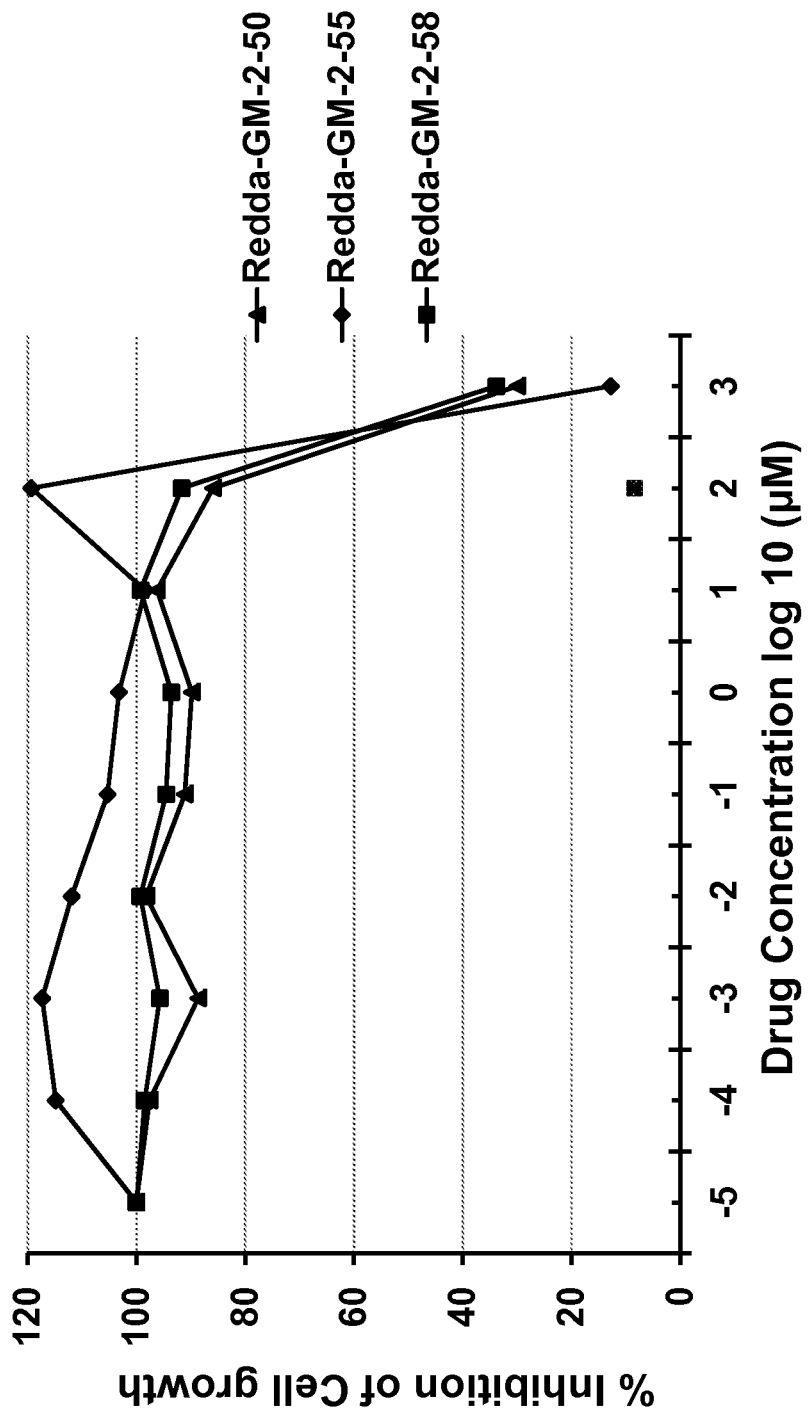
FIG. 4 is a graph illustrating the inhibition of the growth of MDA-MB-231 cells by exposure to the compounds of the disclosure, and to tamoxifen.
Figure 5:
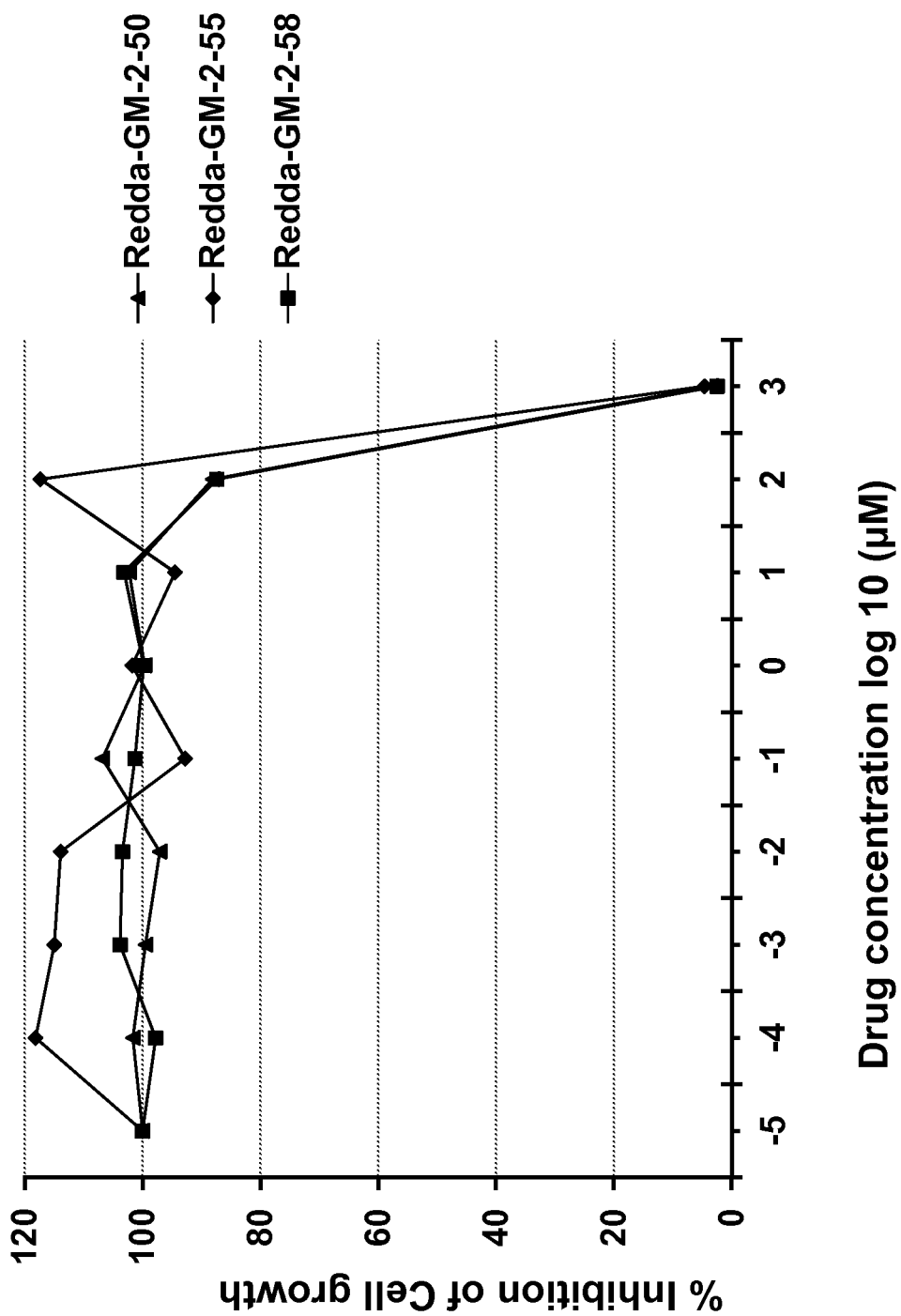
FIG. 5 is a graph illustrating the inhibition of the growth of Ishikawa cells by exposure to the compounds of the disclosure, and to tamoxifen.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and embodiments. It is intended that all such additional systems, methods, features, and advantages be included within this description, be within the scope of the present disclosure.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

The term "sulfonyl", whether used alone or linked to other terms such as alkylsulfonyl or arylsulfonyl, denotes respectively divalent radicals —SO$_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$).

The term "carbonyl", whether used alone or with other terms, such as "aminocarbonyl", denotes —(C=O)—.

The term "substituted acid chloride" as used herein refers to compounds having the general formula of R—(C=O)—Cl, wherein R—(C=O) denotes a substituted carbonyl such as, but not limited to, an alkylcarbonyl, an arylcarbonyl, a heterocyclylcarbonyl, an aminocarbonyl, an N-alkylaminocarbonyl, an N,N-dialkylaminocarbonyl, an N-arylaminocarbonyl, and the like.

The terms "alkylcarbonyl" denotes carbonyl radicals which have been substituted with an alkyl radical. Advantageous are "lower alkylcarbonyl" having lower alkyl radicals as described above attached to a carbonyl radical.

The terms "arylcarbonyl" denotes carbonyl radicals substituted with an aryl radical. Advantageous are "optionally substituted phenylcarbonyl" radicals.

The terms "heterocyclylcarbonyl" denotes carbonyl radicals substituted with an heterocyclyl radical. More preferred are "optionally substituted 5-6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula H$_2$NC=O—.

The terms "N-alkylaminocarbonyl" and "N,N-dialkylaminocarbonyl" denote aminocarbonyl radicals which have been substituted with one alkyl radical and independently with two alkyl radicals, respectively. Advantageous are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. Advantageous aminoalkyl radicals are "lower aminoalkyl" radicals having one to six carbon atoms and one or more amino radicals. Examples of such radicals include aminomethyl, aminoethyl, aminopropyl, aminobutyl, and aminohexyl.

The term "cancer", as used herein shall be given its ordinary meaning and is a general term for diseases in which abnormal cells divide without control. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

The term "alkyl" as used herein refers to saturated monovalent hydrocarbon groups having straight, branched, or cyclic moieties (including fused and bridged bicyclic and spirocyclic moieties), or a combination of the foregoing moieties. For an alkyl group to have cyclic moieties, the group must have at least three carbon atoms.

The term "composition" as used herein encompasses a product comprising the specified ingredients in the specified amounts, as well as any product that results, directly or indirectly, from combinations of the specified ingredients in the specified amounts.

The term "pharmaceutically acceptable salt" as used herein includes, but is not limited to, the acid addition salts of compounds of the present disclosure that are formed with inorganic acids (e.g., hydrochloric acid or phosphoric acids) and organic acids (e.g., acetic, oxalic, tartaric, or maleic acid). Salts formed with the free carboxyl groups may also be derived from inorganic bases (e.g., sodium, potassium, ammonium, calcium, or ferric hydroxides), and organic bases (e.g., isopropylamine, trimethylamine, 2-ethylamino-ethanol, histidine, and procaine).

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "effective amount" and therapeutically-effective amount" as used herein means that amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "subject" and "subject animal or human" as used herein refers to any animal, including a human, to which a composition according to the disclosure may be delivered or administered.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

Discussion

The present disclosure encompasses embodiments of a family of compounds comprising an N-aminopyrrolylmethyltetrahydropyridine group and which have been shown to be effective in inhibiting the proliferation of animal cells. The compounds of the disclosure are advantageous for inhibiting the proliferation of cancer cells, including, but not limited to, breast cancer cells. The potency of the compounds of the disclosure has also shown to be greater than the anti-cell proliferative activity of tamoxifen.

The present disclosure encompasses embodiments of derivatives of N-aminopyrrolylmethyltetrahydropyridine that have anti-proliferative activity against cells. In particular, although not intending to be limiting, the compounds of the disclosure have been found to be effective in inhibiting the proliferation of cancer cells, such as cancer cells that originated in breast tissue. Accordingly, it is contemplated that the compounds of the disclosure may be formulated into pharmaceutically effective compositions for delivery of the anti-proliferative compound to a cultured or in vivo cell, thereby reducing the proliferation rate of the cell or population of cells compared to the proliferation rate of cells not exposed to the compound.

In particular, the compounds of the disclosure may be synthesized according to a schema as illustrated in FIG. 1, and as disclosed in Examples 1-3. It is contemplated in step (iv) of the illustrated schema, the substituted aryl acyl/sulfonyl chloride may include any desired substituent such as, but not limited to, H, a straight-chain alkyl, a branched chain alkyl, a halogen, or an electronegative group such as a nitro group. It is further contemplated that the aryl group of the substituted aryl acyl/sulfonyl chloride may be substituted at any of the positions 2-6 relative to the carbonyl or sulfonyl group but that an advantageous substitution is at the 4-position.

The compounds herein disclosed are analogs that maintain the integrity of the N-aminopyrrolylmethyltetrahydropyridine moiety, and have modifications on the phenyl rings by introducing groups with various electronic properties. The compounds were synthesized and then characterized using NMR, IR and elemental analysis.

The derivatives were examined for their cytotoxic effects on MCF-7 estrogen receptor-positive breast cancer cells, MDA-MB-231 estrogen receptor-negative breast cancer cell line, and Ishikawa cells, using the CELLTITER-GLO (CTG)® luminescent cell viability assay. All the compounds are tested in the three cell lines. Different concentration of compounds, ranging from about 0.01 nM to about 100,000 nM were delivered to $5 \times 10^3$ cells per well, which were then incubated for three days at 37° C., followed by the CTG assay. $IC_{50}$ values were generated, as shown in Table 1. These experiments showed that the compounds of the disclosure had $IC_{50}$ values against the target breast cancer cells that were 6-10-fold less than a currently clinically available and widely-used anti-breast cancer therapy, tamoxifen.

Accordingly, it is contemplated that the compounds of the present disclosure can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present disclosure with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

The compounds of the present disclosure can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present disclosure can exist in different stereoisomeric forms by virtue of the presence of asymmetric centers in the compounds. It is contemplated that all stereoisomeric forms of the compounds as well as mixtures thereof, including racemic mixtures, form part of this disclosure. In addition, the compounds of the present disclosure can exist in unsolvated as well as solvated forms with pharmaceutically acceptable solvents such as water, ethanol, and the like. In general, the solvated forms are considered equivalent to the unsolvated forms for the purposes of the present disclosure.

One aspect of the disclosure encompasses embodiments of a compound having the structure of formula I:

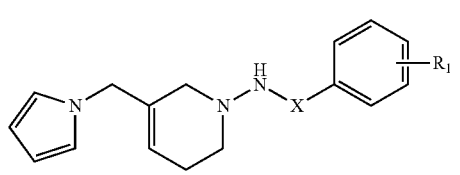
(I)

where X is a carbonyl group or a sulfonyl group; and $R_1$ can be H, an alkyl group, an alkoxy group, or an electronegative group; or a salt thereof.

In embodiments of this aspect of the disclosure, $R_1$ can be $CH_3$ or —O—$CH_3$.

In embodiments of this aspect of the disclosure, $R_1$ can be a halogen or —$NO_2$.

In one embodiment of this aspect of the disclosure, $R_1$ can be $CH_3$.

In one embodiment of this aspect of the disclosure, the compound can be selected from the group consisting of:

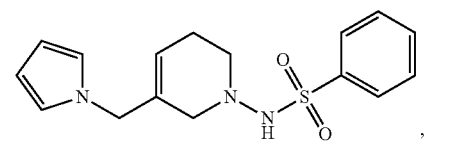
(10a)

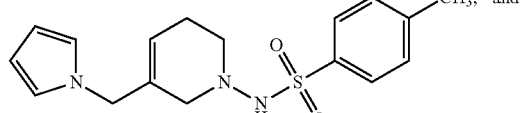
(10b)

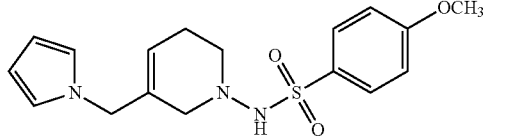
(10c)

Another aspect of the disclosure encompasses embodiments of a pharmaceutically acceptable composition comprising a compound having the structure:

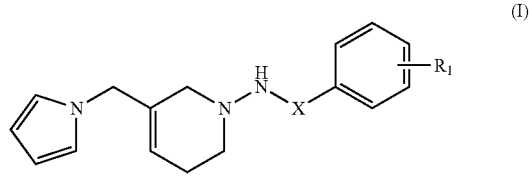
(I)

where X is a carbonyl group or a sulfonyl group; and $R_1$ can be H, an alkyl group, an alkoxy group, or an electronegative group; or a salt thereof, and a pharmaceutically acceptable carrier.

In embodiments of this aspect of the disclosure, $R_1$ can be $CH_3$ or —O—$CH_3$.

In embodiments of this aspect of the disclosure, $R_1$ can be a halogen or —$NO_2$.

In one embodiment of this aspect of the disclosure, $R_1$ can be $CH_3$.

In one embodiment of this aspect of the disclosure, the compound can be selected from the group consisting of:

In one embodiment of this aspect of the disclosure, the pharmaceutically acceptable composition can be formulated to provide an amount of the compound effective in inhibiting the proliferation of a cell cultured in vitro.

In embodiments of this aspect of the disclosure, the cell is a cancer cell.

In some embodiments of this aspect of the disclosure, the cell is a breast cancer cell.

In one embodiment of this aspect of the disclosure, the pharmaceutically acceptable composition can be formulated to provide a therapeutically effective amount of the compound for inhibiting the proliferation of a cell in vivo.

In some embodiments of this aspect of the disclosure, the cell is a cancer cell.

In one embodiment of this aspect of the disclosure, the cell is a breast cancer cell.

Still another aspect of the disclosure encompasses embodiments of a method of inhibiting the proliferation of a cell comprising contacting a cell with an effective amount of a compound having the structure:

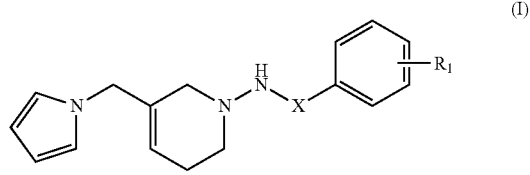
(I)

where X is a carbonyl group or a sulfonyl group; and $R_1$ can be H, an alkyl group, an alkoxy group, or an electronegative group; or a salt thereof, and a pharmaceutically acceptable carrier, thereby reducing the proliferation rate of the cell compared to the proliferation rate of a cell not in contact with the compound.

In embodiments of this aspect of the disclosure, $R_1$ can be $CH_3$ or —O—$CH_3$.

In embodiments of this aspect of the disclosure, $R_1$ can be a halogen or —$NO_2$.

In one embodiment of this aspect of the disclosure, $R_1$ can be $CH_3$.

In embodiments of this aspect of the disclosure, the compound is selected from the group consisting of:

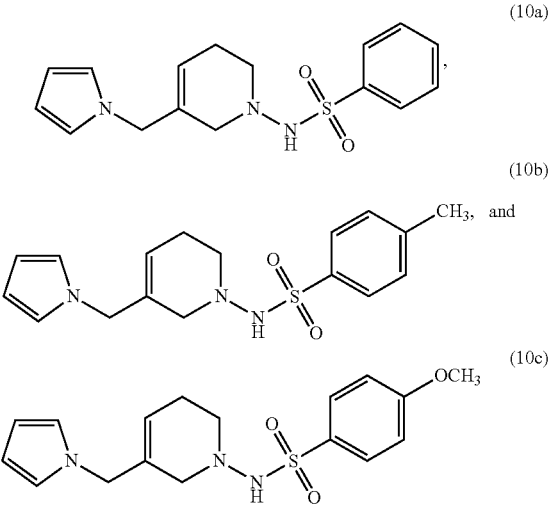

In embodiments of this aspect of the disclosure, the cell can be a cancer cell.

In one embodiment of this aspect of the disclosure, the cell is a breast cancer cell.

In embodiments of this aspect of the disclosure, the cell is a cultured cell or a cell of an animal or human subject.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Synthesis of 3-((1H-pyrrol-1-yl)methyl)-1-(phenylsulfonimido)pyridinium Ylide (10a) (Redda-GM-2-50)

To an ice cooled solution of 3-((1H-pyrrol-1-yl)methyl)pyridine (2.94 g, 18.58 mmol) in 25 mL of dry methylene chloride was added drop wise to O-mesitylenesulfonylhydroxylamine (4.0 g, 18.58 mmol) in 10 mL of dry methylene chloride over 5 min with stirring. The reaction was stirred at 0° C. for 3 hrs. 60 mL of ether was added and the suspension filtered. The precipitate was recrystallized from ethyl acetate-methanol (5:1 v/v) to give 3-((1H-pyrrol-1-yl)methyl)-1-aminopyridinium mesitylenesulfonate (8) in 57.5% yield. The N-Aminopyridinium salt (1.5 g, 4.02 mmol) in 30 ml of anhydrous tetrahydrofuran (THF) containing triethylamine at 70° C. was stirred for 5 min before benzenesulfonyl chloride (0.78 g, 4.42 mmol) was added. The mixture was allowed to proceed for 12 hrs. 70 mL of saturated sodium bicarbonate (NaHCO$_3$) arrested the reaction. The product (10a) was extracted twice with 100 ml of chloroform and dried over anhydrous sodium sulfate, followed by filtration. Solvent was removed in vacuo to give the crude product, which was further purified by column chromatography (2.5×22 cm) on silica gel (200-425 mesh) using ethyl acetate:methanol (9:1 v/v) as eluent. The resultant product was obtained as a light yellow crystalline solid in 43.9% yield.

$^1$HMNR (CDCl$_3$): δ 5.20 (s, 2H, —CH$_2$), 6.26 (t, 2H, J=5.7 Hz, C$_3$', C$_4$'—H), 6.70 (t, 2H, J=2.1 Hz, C$_2$', C$_5$'—H), 7.34-7.44 (m, 4H, C$_3$'', C$_4$'', C$_5$'', C$_5$—H), 7.49-7.50 (dd, 1H, J=1.8, 1.2 Hz, C$_4$—H), 7.66-7.69 (m, 2H, C$_2$'', C$_6$''—H), 8.16 (s, 1H, C$_2$—H), 8.34 (d, 1H, J=3.0 Hz, C$_6$—H).

Example 2

Synthesis of 3-((1H-pyrrol-1-yl)methyl)-1-(4-methylphenylsulfonamido)pyridinium Ylide (10b) (Redda-GM-2-55)

The compound 10b was obtained following General Procedure 1 as off-white solid obtained in 63.7% yield.

$^1$HMNR (CDCl$_3$): δ 2.38 (S, 3H, —CH$_3$), 5.11 (s, 2H, —CH$_2$), 6.22 (t, 2H, J=1.8 Hz, C$_3$', C$_4$'—H), 6.56 (t, 2H, J=1.8 Hz, C$_2$', C$_5$'—H), 7.15-7.18 (dd, 2H, J=8.1, 0.6 Hz, C$_3$'', C$_5$''—H), 7.46-7.48 (dd, 2H, J=5.2, 1.2 Hz, C$_2$'', C$_6$''—H), 7.57-7.60 (dd, 2H, J=4.8, 1.5 Hz, C$_5$, C$_4$—H), 8.16 (s, 1H, C$_2$—H), 8.34 (d, 1H, J=2.7 Hz, C$_6$—H).

Example 3

Synthesis of 3-((1H-pyrrol-1-yl)methyl)-1-(4-methoxyphenylsulfonamido)pyridinium Ylide (10c) (Redda-GM-2-58)

The compound 10c was obtained following General Procedure 1 as off-white solid obtained in 60.0% yield.

$^1$HMNR (CDCl$_3$): δ3.81 (s, 3H, —OCH$_3$), 5.15 (s, 2H, —CH$_2$), 6.22 (t, 2H, J=2.4 Hz, C$_3'$, C$_4'$—H), 6.56 (t, 2H, J=2.1 Hz, C$_2'$, C$_5'$—H), 6.83-6.86 (dd, 2H, J=4.5, 2.1 Hz, C$_3'''$, C$_5'''$—H), 7.46-7.48 (dd, 2H, J=3.9, 0.6 Hz, C$_2''$, C$_6'$—H), 7.62-7.65 (dd, 2H, J=4.5, 2.1 Hz, C$_5$, C$_4$—H), 8.18 (s, 1H, C$_2$—H), 8.35 (d, 1H, J=3.0 Hz, C$_6'$—H).

Example 4

Compounds Redda-GM-2-50, Redda-GM-2-55, and Redda-GM-2-58 were tested for their cytotoxic effects on MCF-7 estrogen receptor-positive breast cancer cells, MDA-MB-231 estrogen receptor-negative breast cancer cell line, and Ishikawa cells, using the CELLTITER-GLO® luminescent cell viability assay (Promega, Madison, Wis.) following the manufacturer's instruction.

CELLTITER-GLO® is a homogeneous method based on the quantification of ATP, which is an indicator of metabolically active cells. In this assay, the number of viable cells in culture is determined based on the quantification of ATP present, which signals the presence of metabolically active cells. Damaged cells are not detected as the ATP leaked from these cells is quickly consumed by ATPases that are also released upon damage). The amount of ATP is determined using a system based on luciferase and D-luciferin resulting in light generation.

The cell lines were plated in 13, 96 well plates at a density of 5000 cells/well in total volumes of 50 µL in phenol-red free medium and incubated for overnight. Compounds Redda-GM-2-50, Redda-GM-2-55, and Redda-GM-2-58 were weighed and dissolved in DMSO (10 mM) and tested at different concentrations ranging from 0.01 to 100,000 nM, using Tamoxifen (10 µM) as a positive control.

25 µL of 40 nM estradiol was added to all appropriate wells on the plate. 25 µL media were added to all wells that did not receive estradiol. 25 µL of stocks (containing the compounds to be tested, DMSO and phenol-red free medium) were added to cells and medium already on plate. 50 µL of medium were added to media wells, and 50 µL of mix (contain 32 mL DMSO+768 mL phenol-red free medium) to all vehicle control wells. Tamoxifen (10 µM) was also added to appropriate wells.

Drug-exposed cells were incubated or 72 h at 37° C. in a 5% CO$_2$ incubator, after which the plates were removed for CELLTITER-GLO® assay and equilibrated at room temperature for 30 min. 100 µL of CELLTITER-GLO® assay reagent was added to each well and cell-lysis was induced on an orbital shaker for 2 min. followed by a 10 min incubation at room temperature. Luminescence results were read on TriLux Luminometer. The luminescent signal was proportional to the number of active cells present in culture. Dead cells did not affect cell counts because they did not contribute to ATP content. As a consequence, the number of metabolically-active cells can be directly derived from the luminescent signal using a specific calibration curve. Data were expressed as percentage of untreated control (i.e. treatment value-blank/vehicle value blank), mean±SE for three replications. The IC$_{50}$ values, as shown in Table 1, were determined using GraphPad Prism 4 dose-response curve fitting.

TABLE I

In vitro Anticancer Activity of Substituted N-aminopyrrolylmethyltetrahydropyridines against Breast Cancer Cell Lines

| Compound | IC$_{50}$ µM | | |
| --- | --- | --- | --- |
| | MCF-7 | MDA-MB-231 | Ishikawa |
| Redda-GM-2-50 | 47.0 | 44.0 | 28.0 |
| Redda-GM-2-55 | 31.8 | 83.6 | 78.5 |
| Redda-GM-2-58 | 49.0 | 53.0 | 28.0 |

We claim:

1. A compound having the structure of formula I:

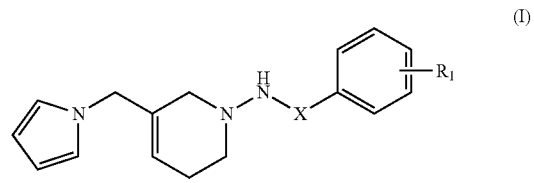

wherein: X is a carbonyl group or a sulfonyl group; and
R$_1$ is H, an alkyl group, an alkoxy group, or an electronegative group; or a salt thereof.

2. The compound of claim 1, wherein R$_1$ is CH$_3$ or —O—CH$_3$.

3. The compound of claim 1, wherein R$_1$ is a halogen or —NO$_2$.

4. The compound of claim 1 selected from the group consisting of:

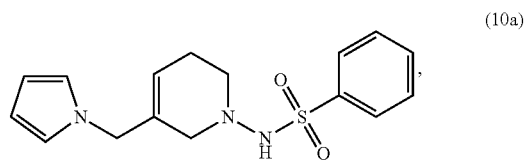

(10a)

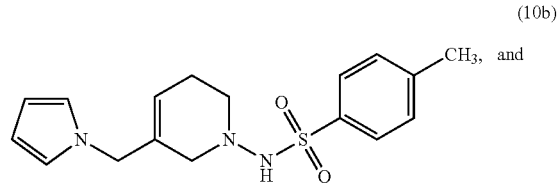

(10b)

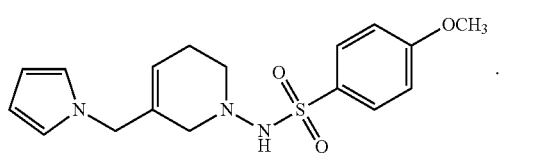

(10c)

5. A pharmaceutically acceptable composition comprising a compound having the structure:

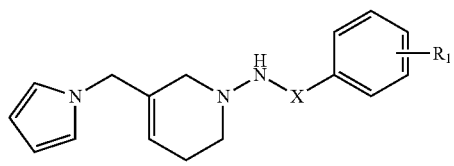
(I)

wherein: X is a carbonyl group or a sulfonyl group; and
R₁ is H, an alkyl group, an alkoxy group, or an electronegative group; or a salt thereof; and
a pharmaceutically acceptable carrier.

6. The pharmaceutically acceptable composition of claim 5, wherein R₁ is CH₃ or —O—CH₃.

7. The pharmaceutically acceptable composition of claim 5, wherein R₁ is a halogen or —NO₂.

8. The pharmaceutically acceptable composition of claim 5, wherein the compound is selected from the group consisting of:

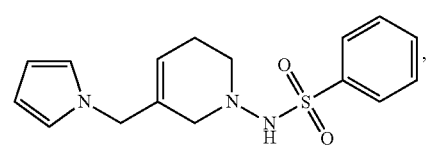
(10a)

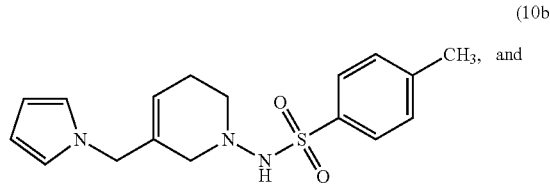
(10b)

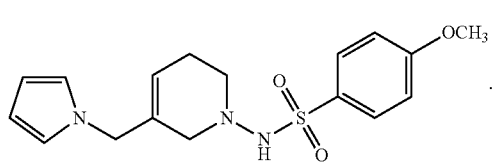
(10c)

9. The pharmaceutically acceptable composition according to claim 5, wherein said pharmaceutically acceptable composition is formulated to provide an amount of the compound effective in inhibiting the proliferation of a breast cancer cell cultured in vitro.

10. The pharmaceutically acceptable composition according to claim 5, wherein said pharmaceutically acceptable composition is formulated to provide a therapeutically effective amount of the compound for inhibiting the proliferation of a breast cancer cell in vivo.

11. A method of inhibiting the proliferation of a breast cancer cell comprising contacting a breast cancer cell with an effective amount of a compound having the structure:

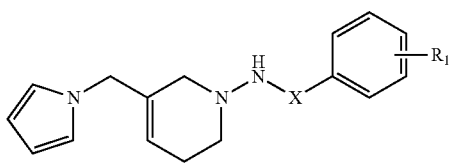
(I)

wherein:
X is a carbonyl group or a sulfonyl group; and
R₁ is H, an alkyl group, an alkoxy group, or an electronegative group; or a salt thereof or a salt thereof, and a pharmaceutically acceptable carrier, thereby reducing the proliferation rate of the cell compared to the proliferation rate of a cell not in contact with the compound.

12. The method of claim 11, wherein R₁ is CH₃ or —O—CH₃.

13. The method of claim 11, wherein R₁ is a halogen or —NO₂.

14. The method of claim 11, wherein the compound is selected from the group consisting of:

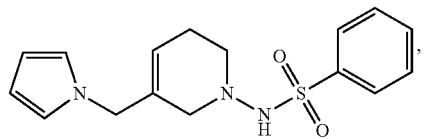
(10a)

(10b)

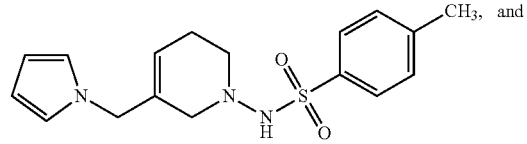
(10c)

15. The method of claim 11, wherein the cell is a cultured cell or a breast cancer cell of an animal or human subject.

* * * * *